United States Patent
Long et al.

(10) Patent No.: US 8,231,630 B2
(45) Date of Patent: Jul. 31, 2012

(54) HUMERAL ROTATING BURR GUIDE

(75) Inventors: Jack F. Long, Warsaw, IN (US);
Stephen R. Donnelly, Willoughby, OH (US)

(73) Assignee: Depuy Products, Inc., Warsaw, IN (US)

( * ) Notice: Subject to any disclaimer, the term of this patent is extended or adjusted under 35 U.S.C. 154(b) by 576 days.

(21) Appl. No.: 12/417,212

(22) Filed: Apr. 2, 2009

(65) Prior Publication Data
US 2009/0264889 A1   Oct. 22, 2009

Related U.S. Application Data

(63) Continuation-in-part of application No. 12/062,952, filed on Apr. 4, 2008, now Pat. No. 8,114,087.

(51) Int. Cl.
*A61F 5/00* (2006.01)
(52) U.S. Cl. .................. 606/87; 606/79; 606/96
(58) Field of Classification Search ............ 30/310, 30/286; 83/565, 574, 746, 745; 408/79; 409/178, 179; 606/87, 79–81
See application file for complete search history.

(56) References Cited

U.S. PATENT DOCUMENTS

| | | |
|---|---|---|
| 5,779,709 A | 7/1998 | Harris et al. |
| 5,779,710 A | 7/1998 | Matsen |
| 5,961,555 A | 10/1999 | Huebner |
| 6,015,437 A | 1/2000 | Stossel |
| 6,102,953 A | 8/2000 | Huebner |
| 6,168,627 B1 | 1/2001 | Huebner |
| 6,193,758 B1 | 2/2001 | Huebner |
| 6,228,120 B1 | 5/2001 | Leonard et al. |
| 6,530,957 B1 | 3/2003 | Jack |
| 6,620,197 B2 | 9/2003 | Maroney et al. |
| 6,673,114 B2 | 1/2004 | Hartdegen et al. |
| 6,780,190 B2 | 8/2004 | Maroney |
| 7,097,663 B1 | 8/2006 | Nicol et al. |
| 7,229,478 B2 | 6/2007 | Masini |
| 7,297,163 B2 | 11/2007 | Huebner |
| 7,338,496 B1 | 3/2008 | Winslow et al. |
| 7,431,736 B2 | 10/2008 | Maroney et al. |
| 7,517,364 B2 | 4/2009 | Long et al. |
| 2004/0002711 A1* | 1/2004 | Berry ............... 606/79 |
| 2004/0034431 A1 | 2/2004 | Maroney et al. |
| 2005/0021038 A1 | 1/2005 | Maroney |

(Continued)

FOREIGN PATENT DOCUMENTS
EP          0687448 A    12/1995
(Continued)

OTHER PUBLICATIONS

European Search Report for Corresponding EPO Application No. 10170055.7-2310 Dated January 10, 2011, 5 Pages.

(Continued)

*Primary Examiner* — Kevin T Truong
*Assistant Examiner* — Olivia C Chang

(57) ABSTRACT

A bone cutting assembly includes a guide pin that may be securely inserted into a bone to define a cutting axis. The bone cutting assembly also includes a housing having a cam surface and features for temporarily fastening the housing to the bone. The bone cutting assembly also includes a burr mounting arm that rotatably and slidably fits onto the guide pin so that the arm can swing around the cutting axis and also translate up and down the guide pin. A user may move the burr mounting arm about the cutting axis so that the arm follows along the cam surface of the housing.

11 Claims, 10 Drawing Sheets

U.S. PATENT DOCUMENTS

| | | |
|---|---|---|
| 2006/0036328 A1 | 2/2006 | Parrott et al. |
| 2006/0276903 A1 | 12/2006 | Maroney et al. |
| 2007/0016305 A1 | 1/2007 | Chudik |
| 2007/0027477 A1 | 2/2007 | Chudik |
| 2007/0100353 A1 | 5/2007 | Chudik |
| 2008/0119861 A1 | 5/2008 | Winslow et al. |

FOREIGN PATENT DOCUMENTS

| | | |
|---|---|---|
| EP | 0893098 A2 | 1/1999 |
| EP | 1464305 A2 | 10/2004 |
| FR | 2731897 A1 | 9/1996 |
| FR | 2863859 A | 4/2008 |
| WO | 2004/075763 A | 9/2004 |
| WO | WO 2005/016123 A2 | 2/2005 |

OTHER PUBLICATIONS

Biomet Orthopedics, Inc., Copeland/Copeland EAS Humeral Resurfacing Head Surgical Technique—2006.

DePuy, a Johnson & Johnson Company—Global Advantage CTA Humeral Head Design Rationale and Surgical Technique—2000.

European Search Report for Eurpoean Application No. 09157237.0-2310, Dated Aug. 10, 2009, 5 pages.

* cited by examiner

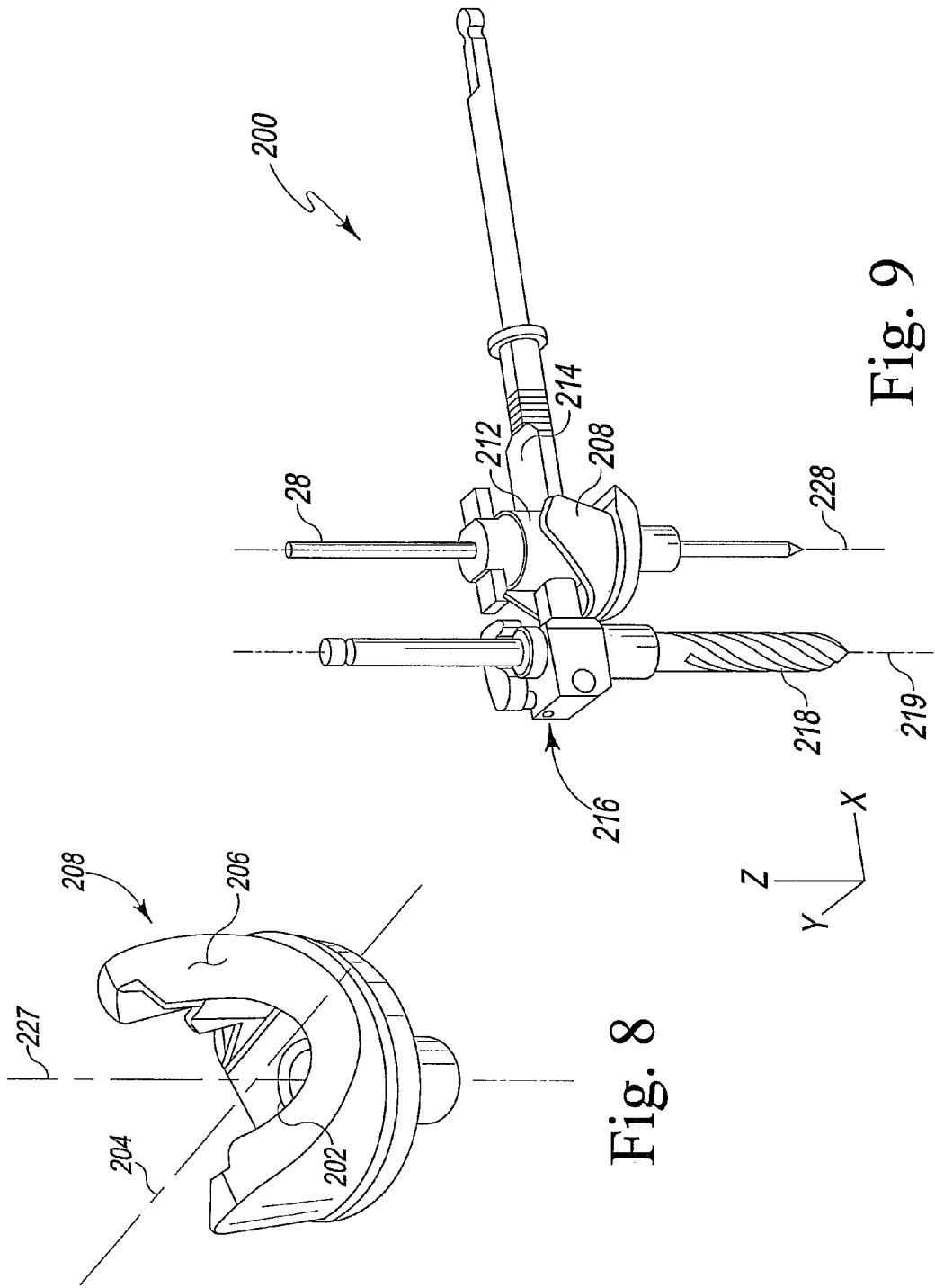

HUMERAL ROTATING BURR GUIDE

RELATED APPLICATIONS

This specification is a continuation-in-part of U.S. patent application Ser. No. 12/062,952 of the same title, filed on Apr. 4, 2008, and issued on Feb. 14, 2012, as U.S. Pat. No. 8,114,087, and herein incorporated by reference in its entirety.

TECHNICAL FIELD OF THE INVENTION

The devices and methods disclosed herein relate generally to the field of orthopaedics, and more particularly, to surgical arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

One type of joint replacement surgery is shoulder arthroplasty. During shoulder arthroplasty, the humeral head must be resected to allow for the insertion of a humeral stem into the intramedullary canal of the humerus. The proximal end of the humerus includes the humeral head, which articulates with the glenoid cavity of the shoulder in a ball and socket fashion. The humeral head is nearly hemispherical in form.

The prostheses typically used for shoulder arthroplasty include a stem portion designed to extend into the intramedullary canal of the humerus and a head portion designed to replace the humeral head. The head portion of the prosthesis extends angularly from the stem portion. The resection of the natural humeral head must be made so that the angle of the cut corresponds to the angle between the stem and head portions of the prosthesis. In addition, the rotation of the cut varies to adjust to bone wear or capsulor looseness.

There are eight essential variables relating to humeral arthroplasty. These include: the diameter of curvature of the prosthesis; the percentage of the sphere with this diameter that will be used as prosthetic articular surface; the superior/inferior position of the articular surface relative to the humerus; the anterior/posterior position of the articular surface relative to the humerus; the medial/lateral articular aspect of the articular surface with respect to the humerus; the anterior/posterior angulation (flexion/extension) of the articular surface relative to the prosthesis; the medial/lateral angulation (varus/valgus) of the prosthesis relative to the humerus; and, the rotational alignment of the prosthetic head with respect to the humeral axis. The goal of prosthetic arthroplasty is to duplicate the normal orientation of the humeral articular surface as well as its diameter of curvature and percentage of the sphere.

Many orthopaedic companies currently provide anatomically variable prosthesis with stems that facilitate adjusting the prosthesis to more accurately reflect the anatomy of the individual. For anatomically variable prostheses, most surgical techniques call for a "freehand" cut of the humeral head. Others have rudimentary guides that facilitate a planar cut but only allow for anterior/posterior (version) or medial/lateral adjustment of the cutting plane.

When the humeral head resection is made free hand, the elbow of the patient is flexed to 90° with the patient's forearm aimed at the midline of the operating surgeon's trunk. The humerus is externally rotated to provide the recommended degree of retrotorsion in relation to the axis of elbow motion. The resection is directed away from the surgeon, allowing the surgeon to reproduce the desired retrotorsion in the bone cut. A trial prosthesis may also be placed along the proximal humeral shaft as a guide for the proper inclination of the resection. The possibility for error exists with this free hand approach. Inaccurate resection can result in an ill-fitting prosthesis which may cause complications for the patient and may eventually require replacement of the prosthetic device.

Also, when implanting a proximal humeral resurfacing implant with an extended articulation surface, removal of part or all of the humeral greater tubercle is needed. This removal should allow for proper fitting and fixation of the implant and the extended articulation surface to the resurfaced humeral head and requires cutting in two planes. However, current cutting guides only allow for the cutting of the humeral greater tubercle in one plane at a time. Therefore, the surgeon would need to perform at least two cutting steps (and possibly use two different tools) to properly prepare the humerus. There is a need for a cutting guide that allows for a surgeon to be able to properly remove the humeral greater tubercle in a single step.

SUMMARY OF THE INVENTION

According to one embodiment of the present invention, a cutting guide for removal of bone during arthroplasty is provided. The cutting guide includes a housing having a three-dimensional guide path as well as an arm coupled to the housing. The arm extends through the guide path and includes a burr. As the arm is slid along the path, the burr simultaneously cuts in two planes.

According to another embodiment of the present invention, a method for resecting a portion of a bone in arthroplasty is provided. The method includes providing a housing having a three-dimensional guide path. An arm is placed in the housing, such that the arm is movable along the three-dimensional guide path. The arm is coupled to the burr. The method also includes simultaneously resecting a portion of the bone in a plurality of planes with the burr.

According to yet another embodiment of the present invention, a cutting guide for cutting a form of a head of a bone during arthroplasty is provided. The cutting guide includes a housing adapted to be placed on the head of the bone and an arm rotatably coupled to the housing. A burr is coupled to the arm such that the burr is adapted to cut the from of the bone as the arm rotates about the housing.

According to another, alternative embodiment of the present invention, a bone cutting assembly includes a guide pin having a distal tip that may be securely inserted into a bone to define a cutting axis. The assembly also includes a housing having a cam surface and features for temporarily securing the housing to the bone. The assembly further includes a burr mounting arm that rotatably and slidably fits onto the guide pin so that the burr mounting arm can swing around the cutting axis and also translate up and down the guide pin. The burr mounting arm acts against the cam surface as it is swung around the guide pin, so that the arm is caused to move up or down relative to the guide pin by the action of the cam surface.

BRIEF DESCRIPTION OF THE DRAWINGS

For a more complete understanding of the present invention and the advantages thereof, reference is now made to the following description taken in connection with the accompanying drawings, in which:

FIG. 8 is a detailed view of a housing of the embodiment of a bone cutting assembly shown in FIG. 9;

FIG. 9 is a perspective view of another alternative embodiment of a bone cutting assembly.

DETAILED DESCRIPTION OF THE INVENTION

Figure 1:
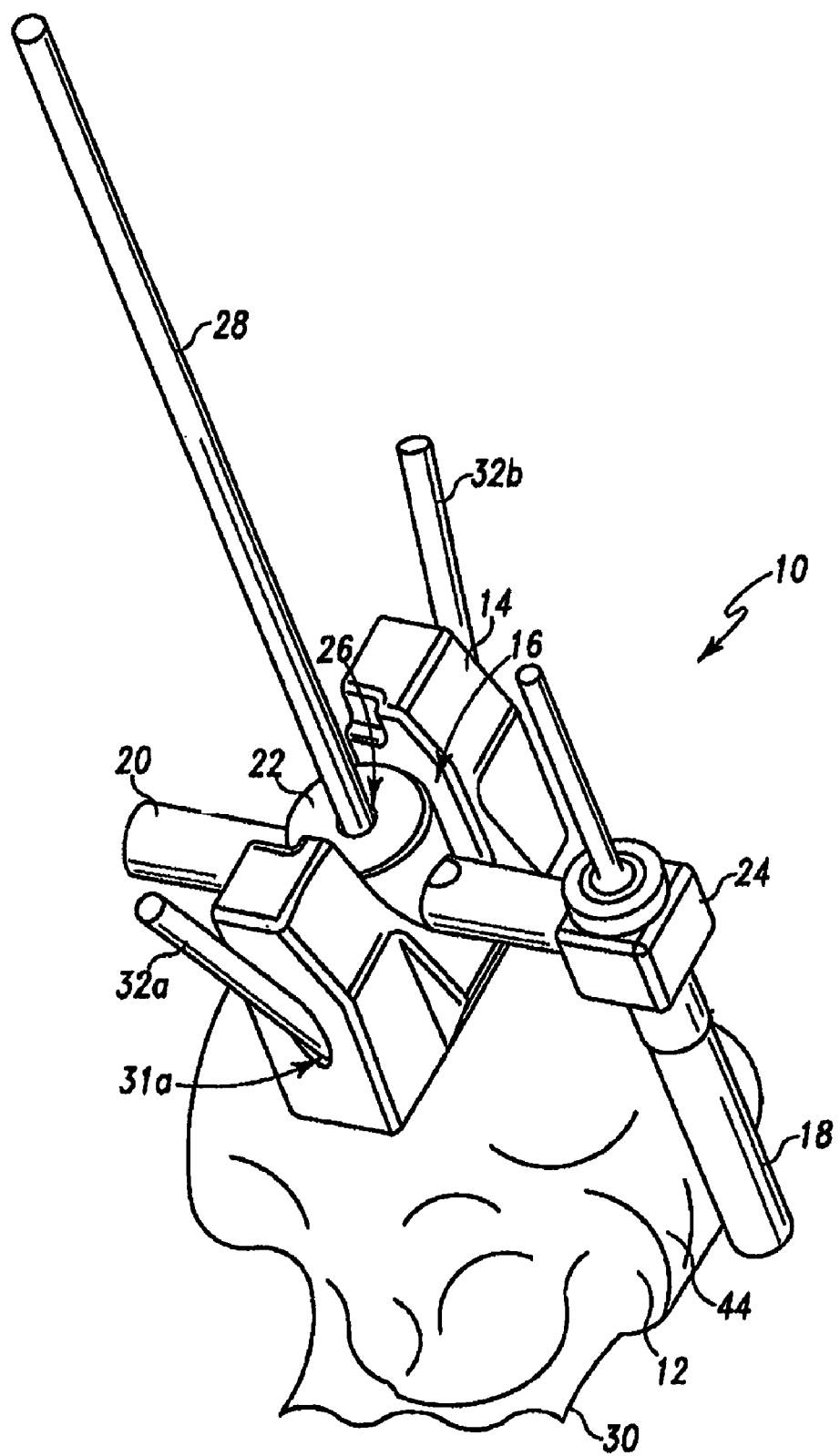
FIG. 1 is a perspective view of a humeral cutting guide on a humerus.

Embodiments of the present invention and the advantages thereof are best understood by referring to the following descriptions and drawings, wherein like numerals are used for like and corresponding parts of the drawings.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
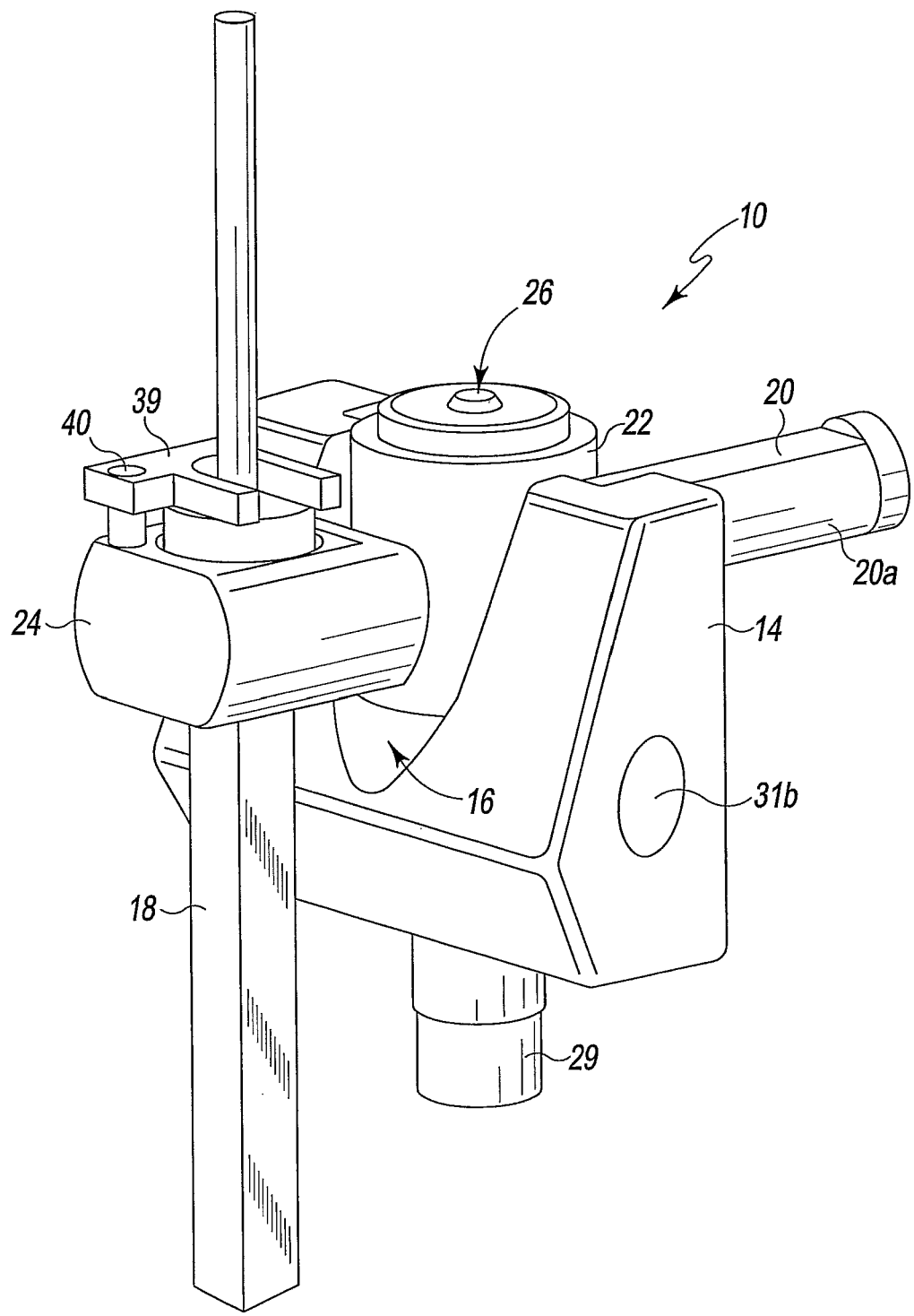
FIG. 2 is a perspective view of the humeral cutting guide of FIG. 1.

Referring now to FIGS. 1 and 2, a cutting guide 10 is provided that allows for the cutting of a humeral head 12. The cutting guide 10 is used to remove a portion of the humeral head 12 to allow for the placement of an implant (not shown). The cutting guide 10 includes a housing 14. The housing 14 includes a three-dimensional guide path, such as a slanted parabolic slot 16 for coupling to a burr 18. The slot 16 extends longitudinally and laterally. The slot 16 defines the path that the burr 18 will cut. The multi-directional nature of the slot 16 enables the burr 18 to move both in the proximal/distal plane and also the medial/lateral plane—thereby allowing for a multiplanar cut.

An arm 20 extends through the slot 16 and includes a burr-attachment end and a quick-connect end. The burr-attachment end is coupled to the burr 18. The arm 20 is held in place in the slot 16 by an adjustable cylinder 22. The arm 20 includes a burr restraint portion 24 that is used to hold the burr 18 on its path. The adjustable cylinder 22 allows the surgeon to adjust the distance between the burr 18 and the housing 14, which will be described in more detail in reference to FIG. 3 below. The quick-connect end 20b of the arm 20 allows the surgeon to hold the burr with one hand while holding a drill portion with the other hand.

The adjustable cylinder 22 includes an opening 26 that extends longitudinally through the adjustable cylinder 22. The opening 26 is adapted to receive a guide pin 28. As shown in FIG. 1, the guide pin 28 extends through opening 26 and a post 29 of the housing 14 into a humerus 30 for holding the cutting guide 10 in place relative to the humeral head 12.

The housing 14 also includes a pair of pin holes 31a, 31b on the sides to align the housing anteriorly and posteriorly on the humeral head 12. Pins 32a, 32b fit through the pin holes 31a, 31b to further affix the housing 14 to the humeral head 12. The pins 32a, 32b prevent the cutting guide 10 from sliding around on the humeral head 12.

Figure 3:
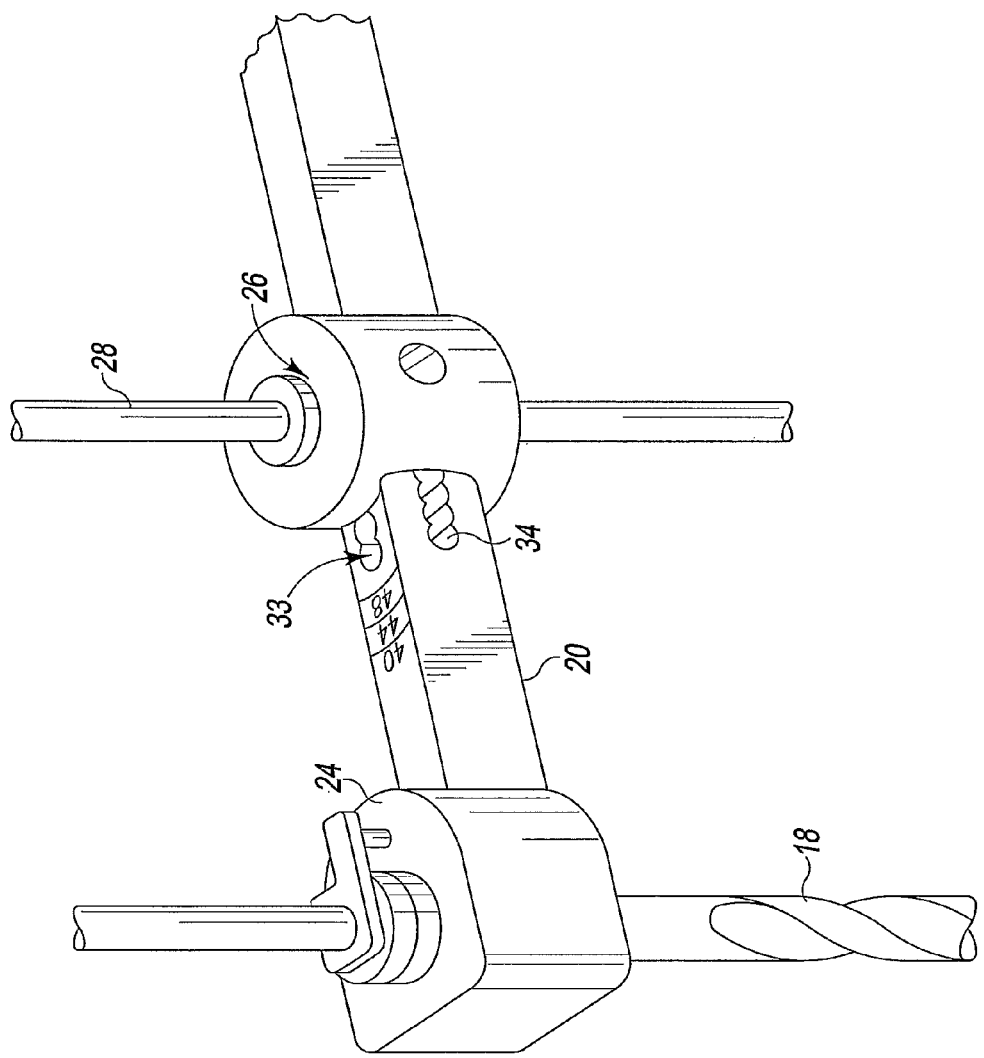
FIG. 3 is a perspective view of a portion of FIG. 2.
Figure 3A:
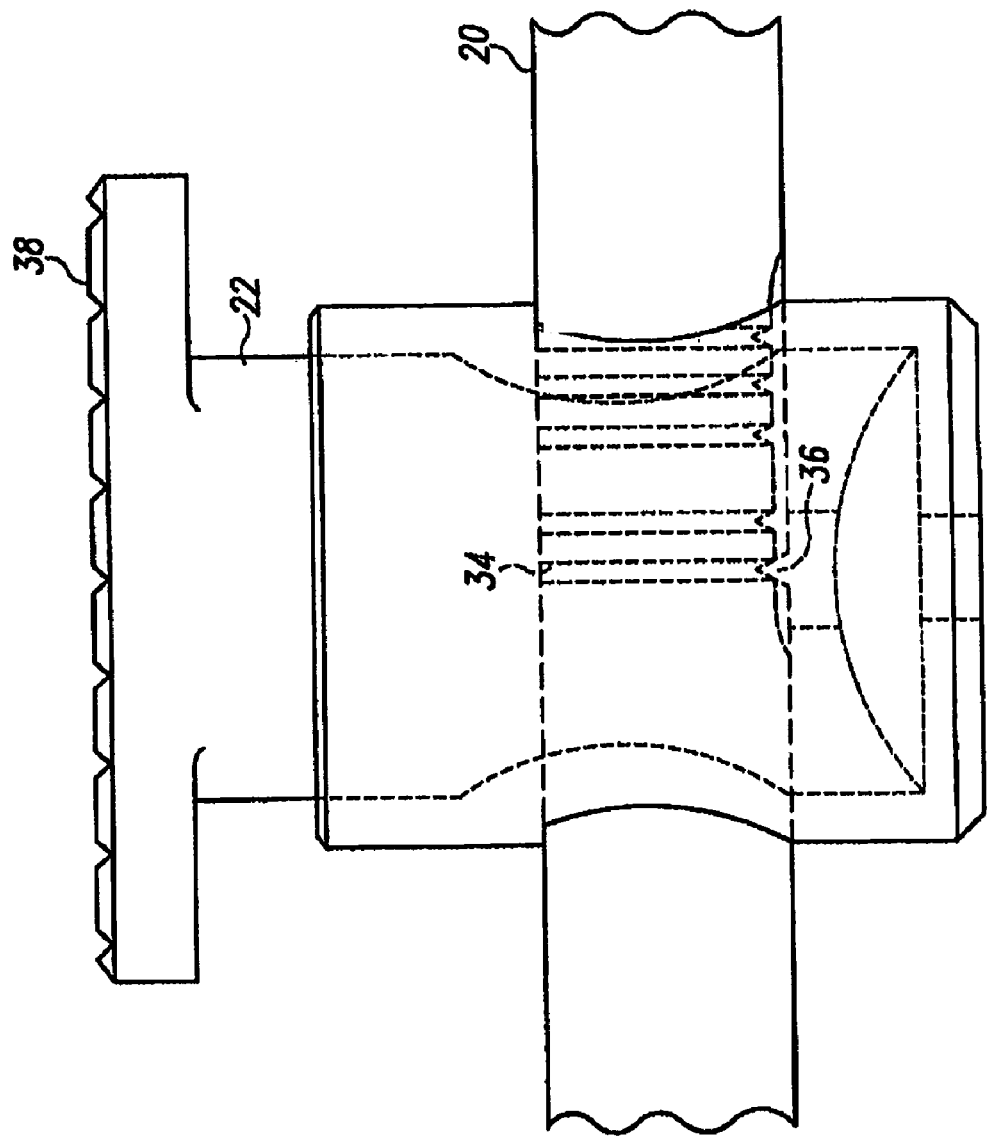
FIG. 3A is a partially see-through view of a portion of the humeral cutting guide of FIG. 1.

Turning now to FIG. 3, a perspective view of the arm 20 is shown. An elongated slot 33 extends through the arm 20. The elongated slot 33 is dimensioned so as to receive the guide pin 28. The arm 20 also includes a plurality of notches 34 that are adapted to correspond with an adjustable pin (not shown). In the embodiment shown in FIG. 3A, the notches 34 extend around the arm 20 and engage a movable ridge 36 on the inside of the adjustable cylinder 22 (FIG. 3A). The ridge 36 couples with one of the notches 34, locking the arm 20 in a particular location relative to the housing 14. A button 38 is included on the top of the adjustable cylinder 22. As best shown in FIG. 3A, when the button 38 is pressed, the ridge 36 disengages the notch 34 so the user can slide the arm 20. In some embodiments of the present invention, the arm 20 may include markings to aid the surgeon in measuring the distance between the cylinder 22 and the burr 18, which will adjust the radius of the cut area.

In an alternative embodiment, the cylinder 22 may include a notch and the arm 20 may include ridges. In other embodiments, other known releasable locking mechanisms may be used.

Returning now to FIG. 2, the restraint portion 24 includes a positioning member 39. The positioning member 39 allows the user to adjust the burr 18 up or down. By being able to adjust the vertical location of the burr 18, the user can control the depth that the burr 18 will cut. The vertically adjustable piece 39 includes a screw 40 that can be adjusted to different heights, allowing the burr 18 to be adjusted.

In another embodiment, the burr 18 may not be vertically adjustable. Instead, there may be provided a plurality of burrs that have different depths, which would allow for different heights to be cut.

Figure 4B:
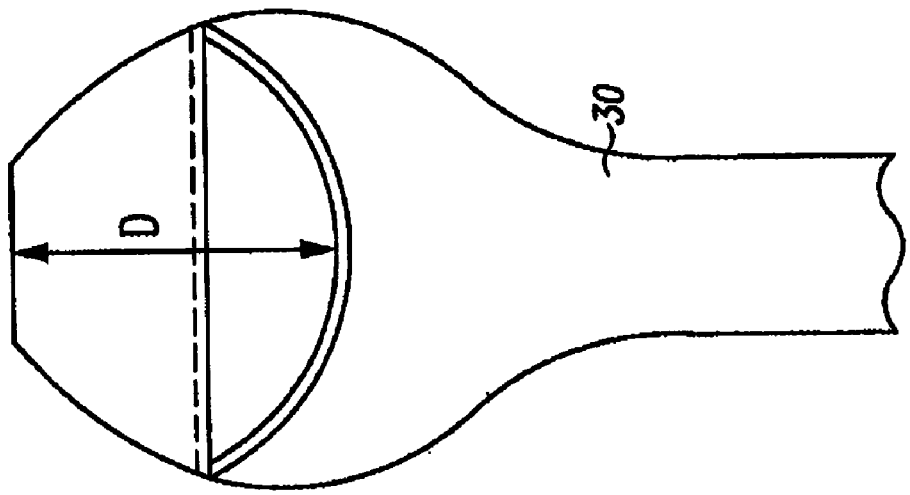
FIG. 4B is a lateral-medial view of a resurfaced humeral head.
Figure 4A:
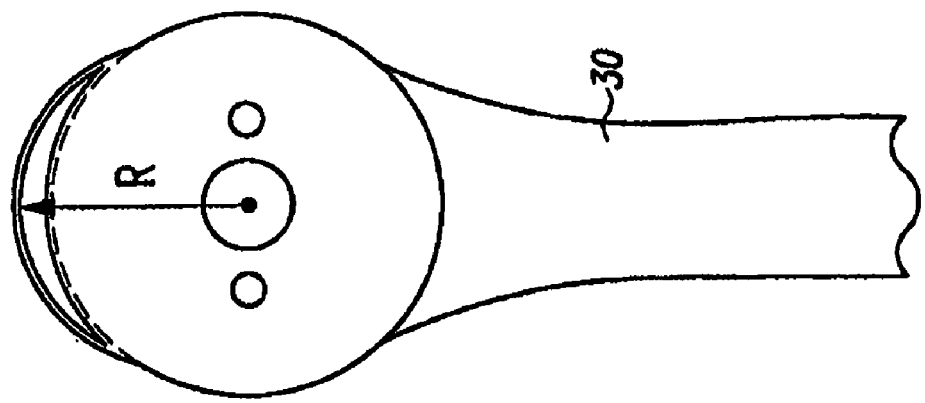
FIG. 4A is a medial-lateral view of a resurfaced humeral head.

FIGS. 4A and 4B show a top and a side view of the humerus 30. As illustrated, the humerus 30 includes a greater humeral tubercle 44 (best seen in FIG. 1) that needs to be either partially or wholly removed. The greater humeral tubercle 44 includes a radius R and a depth D. The cutting guide 10 of the present invention will be able to cut both the radius R and the depth D in a single step, as will be described below.

Figure 5:
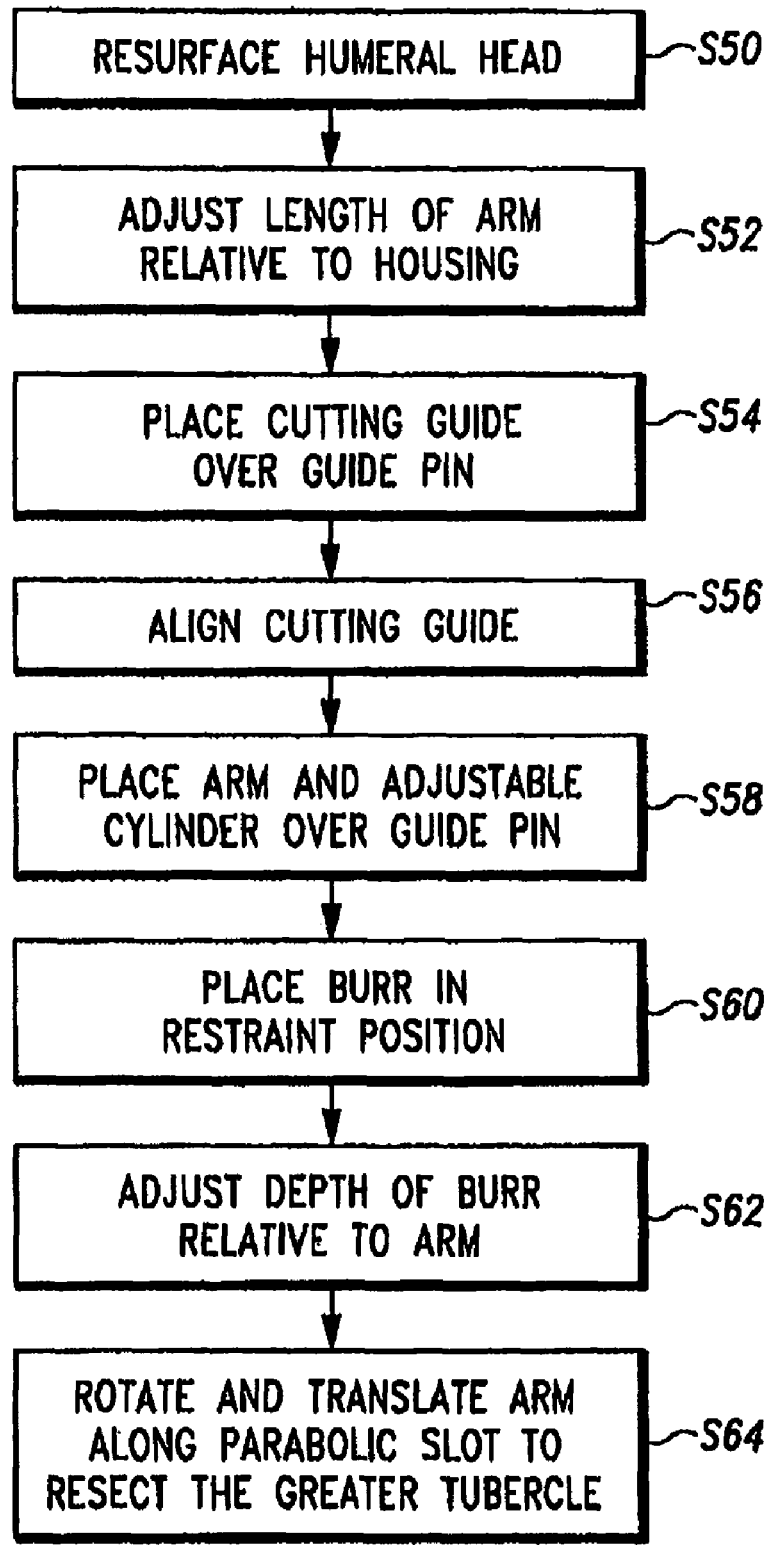
FIG. 5 is a flow chart describing the operation of the humeral cutting guide.

Turning now to FIG. 5, a method for using the cutting guide 10 will be described. First, at step s50, a humeral head 12 is resurfaced using a spherical reamer over the guide pin 28. The reamer allows for a flat surface to be created on the top of the humeral head 12. At step s52, the length of the arm 20 is adjusted to the desired length. Next, at step s54, the cutting guide 10 is placed over the guide pin 28. The housing 14 of the cutting guide 10 sits on the flat on the top of the humeral head 12. The post 29 fits into the reamed hole. Next, at step s56, the cutting guide 10 is aligned using the pin holes 31a, 31b on the housing 14. Pins 32a, 32b are placed in the pin holes 31a, 31b at step s56 to prevent rotation of the housing 14. At step s58, the arm 20 and adjustable cylinder 22 are then placed over the guide pin 28 in the parabolic slot 16 of the housing 20. The burr 18 is then placed into the restraint portion 24 of the arm 20 at step s60. At step s62, the depth of the burr 18 will be adjusted (if so desired). The arm 20 is then rotated and translated along the parabolic slot 16 to resect the radius R and depth D simultaneously on the humerus 30 at step s64. After the required part of the greater tubercle 42 is removed, the cutting guide 10 is then removed from the guide pin 28 and the trialing and implantation of the prosthesis can occur.

In some embodiments, step s52 may take place after the arm 20 is placed over the guide pin 28. In some embodiments, step 62 may not be included. In those embodiments, multiple burrs of different sizes may be included and the surgeon selects one of the burrs depending on the depth the surgeon would like to cut.

By placing the cutting guide 10 on the guide pin 28 that is used in other cutting procedures, reproducible and properly placed cuts can be more easily achieved. Also, because of the three-dimensional parabolic nature of the slot 16, the radius and the depth can be cut simultaneously, allowing for resection in multiple planes. Also, in some embodiments both the arm 20 and the burr are adjustable relative to the housing 14, both the radius and the depth to be cut can be adjusted depending upon the anatomy of the patient or the need of the surgeon.

Figure 6:
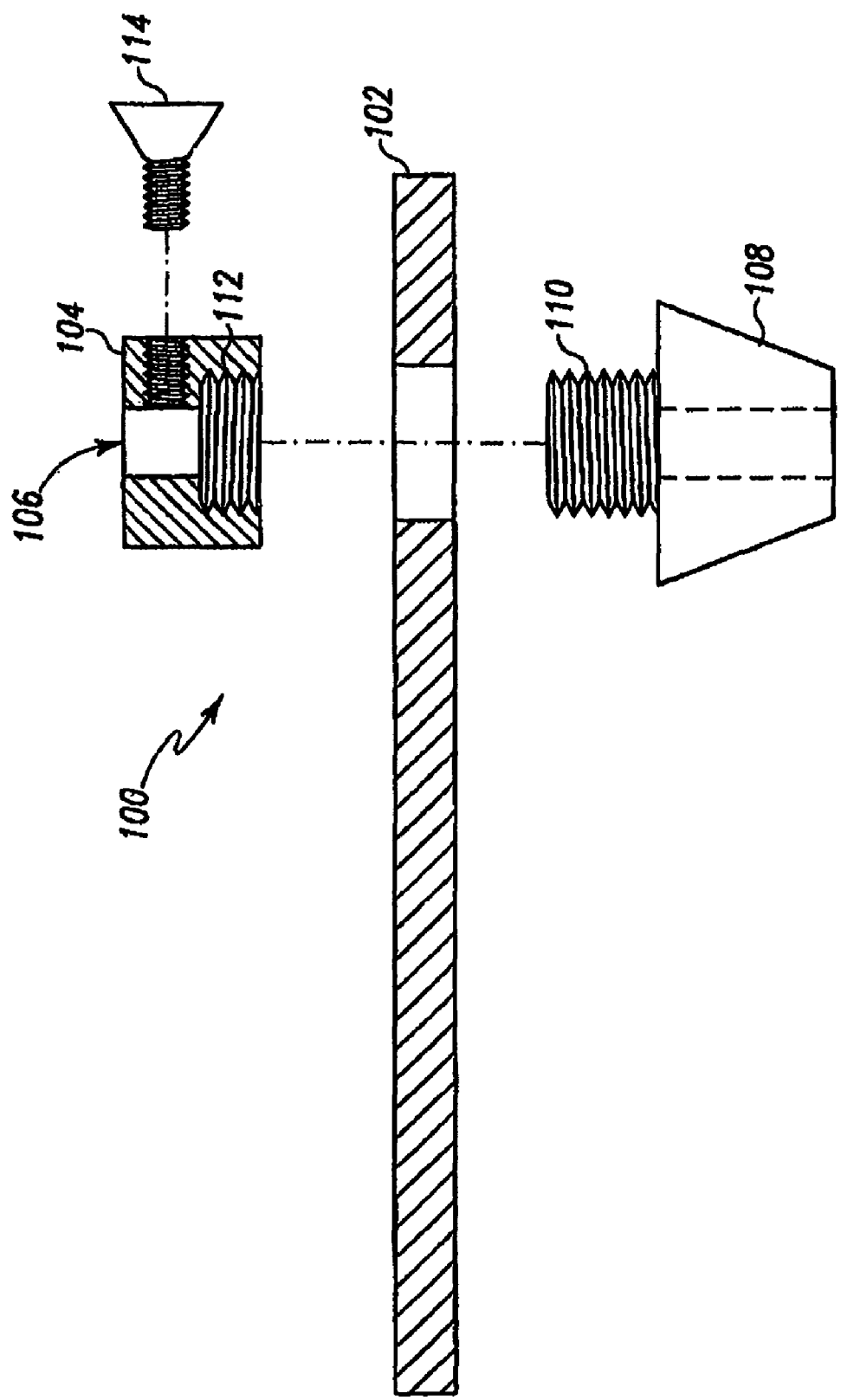
FIG. 6 is perspective view of an alternative embodiment of the present invention.
Figure 7:
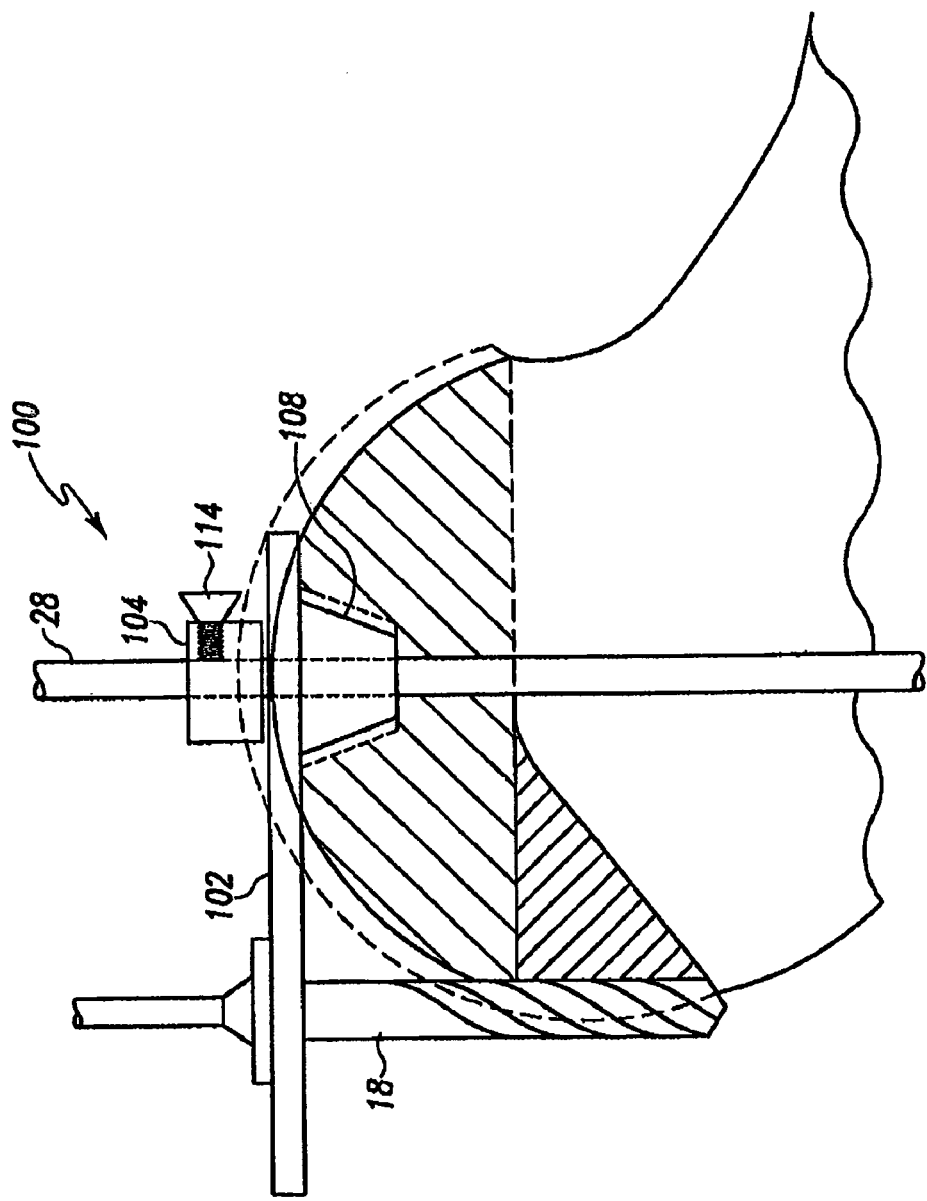
FIG. 7 is an exploded view of the embodiment shown in FIG. 6.

Turning now to FIGS. 6 and 7, another embodiment of the present invention will be described. A cutting guide 100 is provided that includes an arm 102 that couples to the burr 18. The cutting guide 100 further includes a housing 104. The housing 104 includes an opening 106 to enable the housing 104 to slide over the guide pin 28. The cutting guide 100 also includes a stem hole stabilizer 108 that attaches to the housing 104 via a threaded portion 110 as shown in FIG. 6. The threaded portion 110 engages a threaded opening 112 in the housing 104. The housing 104 and stem hole stabilizer 108 can be adjusted vertically relative to the guide pin 28 via a screw 114 that locks the housing in position on the guide pin 28.

In use, the arm 102 swings along a curved path on the humeral head 12, guiding the burr 18. The swinging of the arm 102 causes the burr 18 to cut off a radius of the greater tubercle. In other words, the burr 18 swings along an arcuate path on the greater tubercle. In this embodiment, another cutting guide would need to be used to cut the appropriate depth.

In one embodiment, the burr 18 is made of a stainless steel having a hardness between about 40 and 55 on the Rockwell scale. In embodiments where the burr 18 is only intended to be used once, the burr may be made of a softer metal. In other embodiments, the burr 18 may be made of a softer metal, but may be coated with stainless steel having the hardness described above. The arm 20 may be made of stainless steel or other sterilizable metals. The arm 20 itself may also be a one-time instrument made of a polymer material. The housing 14 may also be made of stainless steel or other sterilizable metal. In other embodiments, the housing may also be made of a polymer material. In the above-described invention, the path cut was an arcuate path that included both a radius and a depth. In other embodiments, the multi-dimensional guide path could be designed so as to cut other dimensions that result in two planes being simultaneously cut. For example, in some embodiments, the path may be a parabolic slot that cuts both a radius and a width. In other embodiments, the path may be of a different shape that cuts an oval or a rectangle while simultaneously cutting another dimension.

FIG. 9 shows another embodiment of a bone cutting assembly 200 for guiding a burr cutting tool 218 having an axis of rotation 219. Bone cutting assembly 200 includes a housing 208, which rotatably receives a mounting cylinder 212, which in turn slidably mounts onto a burr mounting arm 214. Bone cutting assembly 200 may further include a clamp 216 on one end of burr mounting arm 214 for engaging burr cutting tool 218, for example as described above with reference to FIG. 2. Bone cutting assembly 200 also includes guide pin 28 defining a cutting axis 228, about which burr cutting tool 218, mounting cylinder 212 and arm 214 may pivot when the distal end of guide pin 28 is securely positioned into the bone such as the proximal humerus. Burr mounting arm 214 may be fixed against sliding relative to mounting cylinder 212 as described above with reference to FIG. 3A.

Figure 10:
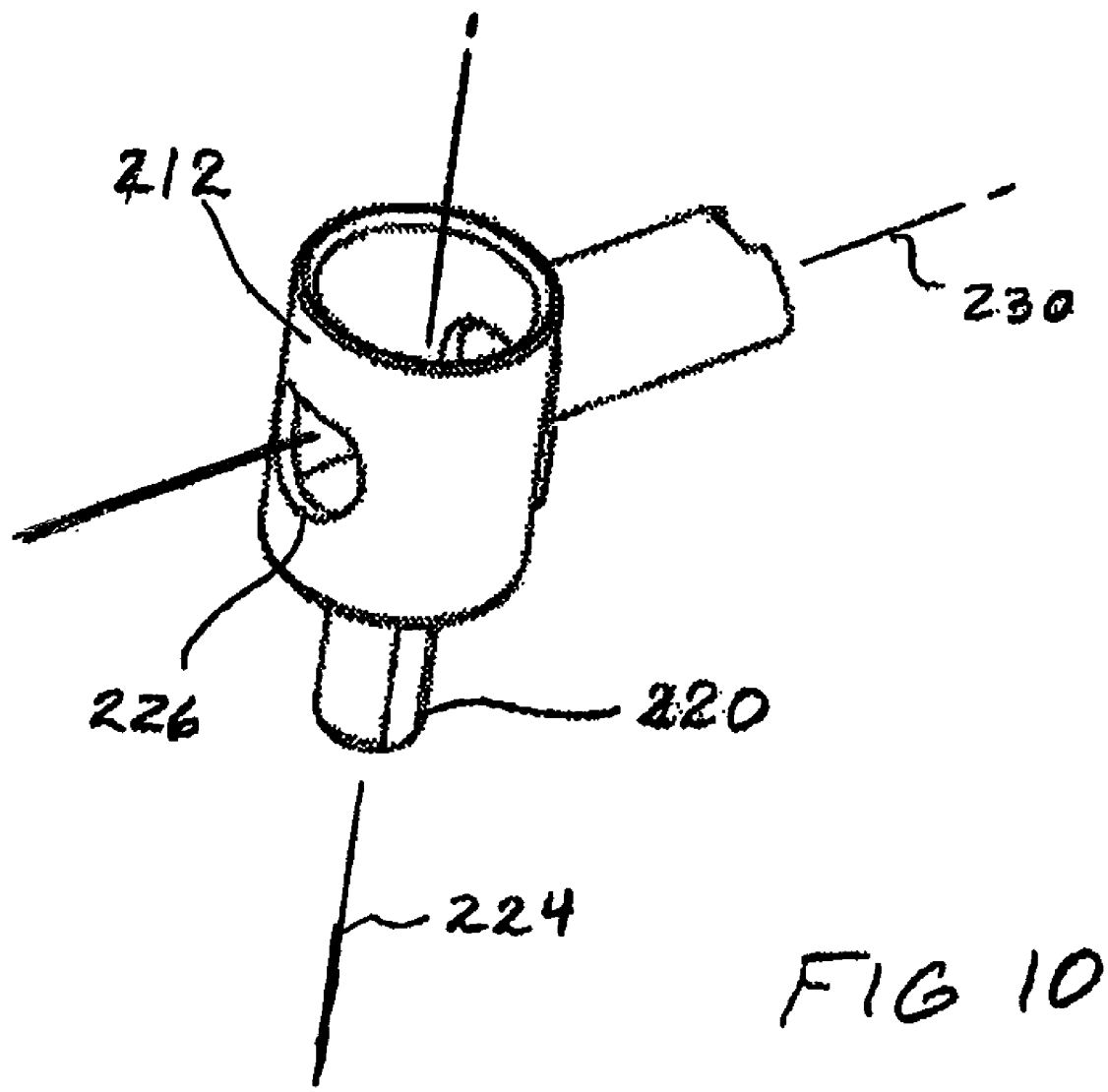
FIG. 10 is a detailed view of a mounting cylinder of the alternative embodiment of the bone cutting assembly shown in FIG. 9.

FIG. 8 and FIG. 10 show detailed views, respectively, of housing 208 and mounting cylinder 212. Housing 208 has a bore 202 sized for slideably and rotatably receiving a boss 220 of mounting cylinder 212 (FIG. 10). Boss 220 has an internal bore (not visible) along axis 224 for passage of guide pin 28. A transverse through-hole 226 of mounting cylinder 212 slidably receives mounting arm 214 along an axis 230.

Housing 208 defines a slot 204 that is perpendicular to bore 202. Slot 204 defines a cam surface 206 that is generally concave and having a parabolic shape, for example, when viewed in the same direction as axis 204. An edge wall 208 is the portion of housing 208 that borders cam surface 206. When viewed from above in the direction of axis 227, edge wall 208 may have the shape of a portion of a circle.

Bone cutting assembly 200 may be used to mill a portion of a bone such as the proximal humerus, for example, in order to seat a humeral prosthesis as previously described. The milled portion of bone generally defines a portion of a cylinder having a radius determined by the adjustment of mounting arm 214 relative to cutting axis 228. The profile and depth of the distal edge of the removed bone, as created by the distal tip of burr cutting tool 218 as it swings about cutting axis 228, is determined by the shape of cam surface 206. This is achieved by swinging burr mounting arm 214, while the rotating, burr cutting tool 218 is retained within clamp 216 at one end of arm 214, around cutting axis 228. As the surgeon moves arm 214 around axis 228, arm 214 follows cam surface 206. The surgeon may grip a control handle (not shown) attached to the end of arm 214 opposite cutting tool 218 to control the movement of arm 214.

Although the above-embodiments have been described being used with a humeral head, it should be understood that the cutting guide of the present invention may be used to cut other bones in preparation of arthroplasty.

Although the present invention and its advantages have been described in detail, it should be understood that various changes, substitutions, and alterations can be made therein without departing from the spirit and scope of the present invention as defined by the appended claims.

We claim:
1. A bone cutting assembly comprising:
   a. a guide pin having a distal tip that may be securely inserted into a bone to define a cutting axis, the guide pin having a longitudinal axis;
   b. a housing having a cam surface and features for temporarily securing the housing to the bone, wherein the cam surface has a parabolic shape when viewed in a direction transverse to the longitudinal axis and the cam surface has a circular shape when viewed from above in the direction of the longitudinal axis;
   c. a burr mounting arm that rotatably and slidably fits onto the guide pin so that the burr mounting arm can swing around the cutting axis and also translate up and down the guide pin;
in which the burr mounting arm acts against the cam surface as it is swung around the guide pin, so that the arm is caused to move up or down relative to the guide pin by the action of the cam surface.

2. The bone cutting assembly of claim 1, wherein the burr mounting arm acts directly against the cam surface.

3. The bone cutting assembly of claim 1, wherein the housing includes a slot defined by the cam surface and extending transverse to the cutting axis, and wherein the burr mounting arm fits within the slot.

4. The bone cutting assembly of claim 1, wherein the burr mounting arm is rotatably movable about the cutting axis through an angle of at least ten degrees.

5. The bone cutting assembly of claim 1, wherein the burr mounting arm is rotatably movable about the cutting axis through an angle of not more than approximately 180 degrees.

6. The bone cutting assembly of claim 1, further comprising a burr cutting tool retained on the burr mounting arm.

7. The bone cutting assembly of claim 6, wherein the burr cutting tool has an axis of rotation that is approximately parallel to the cutting axis defined by the guide pin.

8. The bone cutting assembly of claim 1, further including a mounting cylinder that fits onto the guide pin and that includes a through bore extending transversely to the cutting axis, wherein the through bore slidably and rotatably retains the burr mounting arm.

9. The bone cutting assembly of claim 8, wherein the spacing of one end of the burr mounting arm relative to the mounting cylinder is adjustable.

10. The bone cutting assembly of claim 8, wherein the cam surface, when viewed in the direction of the cutting axis, is shaped like a portion of a circle.

11. The bone cutting assembly of claim 1, wherein the cam surface has a generally concave profile when viewed in a direction transverse to the cutting axis.

* * * * *